(12) United States Patent
Pillonel et al.

(10) Patent No.: US 6,399,319 B1
(45) Date of Patent: Jun. 4, 2002

(54) PROTEIN KINASE ASSAY AS A METHOD FOR IDENTIFICATION OF FUNGICIDES

(75) Inventors: Christian Pillonel, Magden; Thomas Meyer, Basel, both of (CH)

(73) Assignee: Syngenta Crop Protection, Inc., Greensboro, NC (US)

( * ) Notice: Subject to any disclaimer, the term of this patent is extended or adjusted under 35 U.S.C. 154(b) by 0 days.

(21) Appl. No.: 09/194,048

(22) PCT Filed: May 15, 1997

(86) PCT No.: PCT/EP97/02476

§ 371 (c)(1),
(2), (4) Date: Nov. 19, 1998

(87) PCT Pub. No.: WO97/44484

PCT Pub. Date: Nov. 27, 1997

(30) Foreign Application Priority Data

May 23, 1996 (GB) ................................................ 9610872

(51) Int. Cl.[7] ............................ C12Q 1/48; C12N 9/12; A61K 38/45; A01N 63/04
(52) U.S. Cl. ......................... 435/15; 435/194; 424/94.5; 504/117
(58) Field of Search .......................... 435/21, 195, 171, 435/15, 29, 194; 424/1.77, 94.5, 404; 530/358; 504/101, 117

(56) References Cited

U.S. PATENT DOCUMENTS 4,820,692 A * 4/1989 Riscoe et al. .................. 514/23
5,382,675 A * 1/1995 Wacker ....................... 549/420
5,641,627 A * 6/1997 Moehle ......................... 435/6
5,733,920 A * 3/1998 Mansuri et al. .............. 514/337

FOREIGN PATENT DOCUMENTS

| AU | 39284/89 | 2/1990 | |
| EP | 354183 | 2/1990 | ......... A01N/43/653 |
| EP | 446798 | 9/1991 | ......... C07D/213/28 |

OTHER PUBLICATIONS

Judewicz et al., "Protein Kinase Activities in *Neurospora crassa*", Archives of Biochemistry and Biophysics vol. 206 No. 1 Jan. 1981 pp. 87–92.*

Szoor et al. isolation and characterization of the catalytic submit of protein phosphatase 2A from *Neurospora crassa* Comp. Biochem. Physiol. vol. 112B No. 3 pp. 515–522 1995.*

Favre et al. Identification of a calcium and phospholipiddependent protein kinase: Protein kinase C in *Neurospora–crassa*. Plant Science 49 (1), pp. 15–22. (1987). No month found.*

Amersham Life Science catalog, p. 286. (1995) No month found.*

Pillonel et al., Pestic. Sci. 1997, 49, 229–236.

* cited by examiner

Primary Examiner—Michael P. Woodward
Assistant Examiner—Marjorie A Moran
(74) Attorney, Agent, or Firm—William Teoli, Jr.

(57) ABSTRACT

Protein kinase inhibition assays are utilized for identifying new fungicides. An assay for detecting substances having fungicidal activity comprises a protein kinase as enzyme in a buffer system, ATP as a phosphate donor, and a phosphate acceptor together with an appropriate solvent and a device for measuring phosphorylation rates.

8 Claims, 1 Drawing Sheet

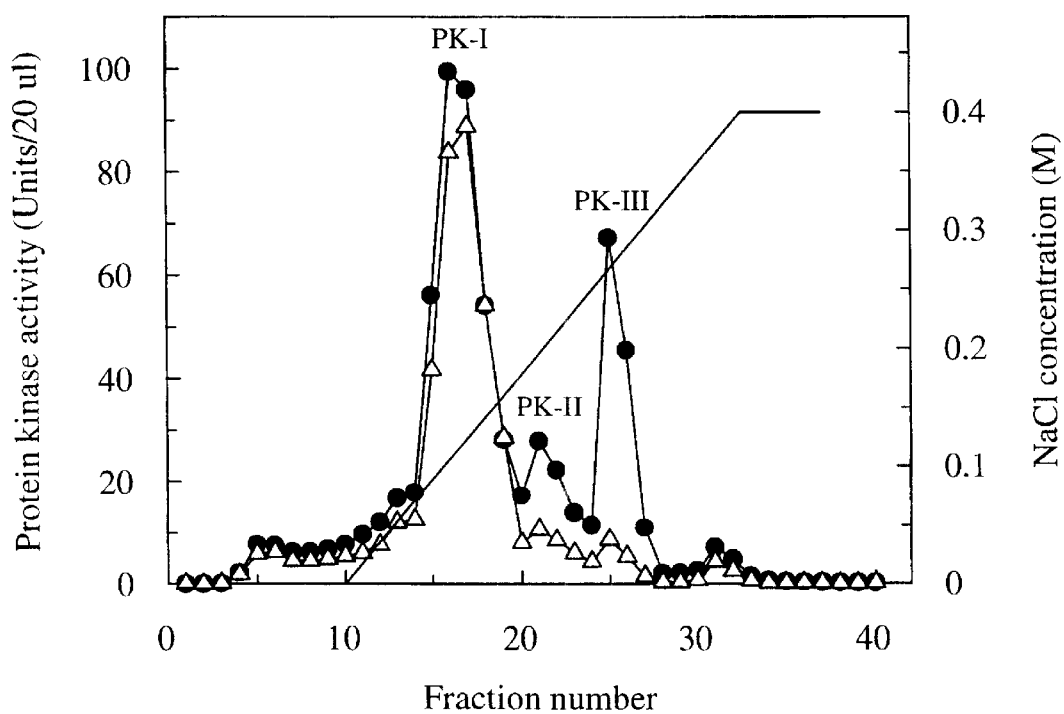

PROTEIN KINASE ASSAY AS A METHOD FOR IDENTIFICATION OF FUNGICIDES

This application is the U.S. filing under 35 USC 371 of PCT/EP97/02476, filed May 15, 1997.

The present invention relates to a novel method which is useful in the field of the identification of fungicides.

Protein phosphorylation has long been recognized as an important event in the regulation of cell differentiation as well as in the generation and the transduction of signals in cells. In spite of this knowledge, selection of antifungals has never been based on the protein kinase inhibitory effect.

The present invention consists in a procedure for the identification of fungal protein kinase inhibitors. The procedure consists in the cultivation of the target fungus up to the logarithmic growth phase, in the isolation of a protein kinase and in the protein kinase activity measurement with various concentrations of inhibitors from a concentrated stock solution.

An objective of the present invention is an assay for detecting substances having fungicidal activities which comprises
 a) a protein kinase as enzyme in a buffer system,
 b) ATP as a phosphate donor, and
 c) a phosphate acceptor,
together with an appropriate solvent and a device for measuring the phosphorylation rates.

In particular prefered is an assay for detecting substances having fungicidal activities which comprises
 a) determining the activity of a protein kinase in the presence of ATP as a phosphate donor and a phosphate acceptor, together with an appropriate solvent and a device for measuring the phosphorylation rates and
 b) selecting substances which inhibit the protein kinase.

A further aspect of the invention is a method for identifying potential fungicides which comprises testing a candidate compound in a protein kinase inhibition assay. Prefered is a method for identifying potential fungicides which comprises
 (a) testing a candidate compound in a protein kinases inhibition assay, and
 (b) if the candidate compound is active in the protein kinase inhibition assay, testing the compound for activity against fungi.

A further aspect of the invention is a fungicide that has been identified by the protein kinase inhibition assay. Comprised is a compound active in a protein kinase inhibition assay according to the invention as a fungicide.

Another aspect of the invention is the use of a compound, which has been identified with a protein kinase inhibition assay, as a fungicide.

A further aspect of the invention is the use of a compound, which inhibits a protein kinase, as a fungicide.

A further aspect of the invention is a fungicide composition comprising a protein kinase inhibitor as the active ingredient in combination with a carrier and/or a second fungicide.

Another aspect of the invention is a fungicide method which comprises applying a fungi inhibiting amount of a protein kinase inhibitor to the locus it is desired to protect from fungi.

It is known that usnic acid amide inhibits protein kinase C (Phytochemistry 31,2999–3001,1992), that certain medicaments shows protein kinase C inhibition (EP-A-446798) and that a serine protein kinase confers fungicide resistance (Applied and Environmental Microbiology, 61,2341–2345, 1995).

It was found that potential fungicides inhibit the protein kinase activity. The inhibition is observed by the measurement of the protein kinase activity as a result of the phosphorylation reaction with a substrate in the presence of the test compound which is being evaluated for fungicidal properties. Protein kinase inhibition assays are utilized in a method for identifying new fungicides.

A test compound can be characterized as having fungicidal properties when one or more of the protein kinases fractions (PK-I, PK-II, PK-III etc) decreases in the activity by the phosphorylation reaction of a substrate compared to the activity observed in the same reaction without the test compound.

Preferred is the use of a test compound in an protein kinase inhibition assay wherein the protein kinase is a protein kinase III from *Neurospora crassa*.

The method consists in the isolation of a protein kinase from a fungus, e.g.*Neurospora crassa*. The fungus is cultivated using standard methods, preferably as inoculum in Petri dishes, up to the logarithmic growth phase.

Protein kinase is isolated using standard methods. The protein kinase extract is then resolved into fractions of a suitable volume, preferably of 2 ml. Further purification is carried out, for example by centrifugation, gel filtration, ion exchange chromatography, affinity chromatography, ammonium sulfate precipitation or combinations thereof.

The collected fractions are submitted to the phosphorylation reaction with a dye-labeled substrate or a non labeled substrate, e.g. casein, histon, protamine-sulfate, protamine free base, kemptide; preferably selected from protamine base or protamine-salt, more preferably with the non labeled protamine-sulfate.

Suitable phosphorylation agents are $[\gamma\text{-}^{33}\text{P}]\text{ATP}$, $[\gamma\text{-}^{32}\text{P}]\text{ATP}$, ATP, preferably radioactive $[\gamma\text{-}^{33}\text{P}]\text{ATP}$.

The reaction is carried out in a suitable polar solvent, e.g. water, ethanol, dimethylsulfoxide, acetone, preferably in dimethylsulfoxide.

The amount of phosphorylated products is determined by conventional methods, e.g. colorimetry, scintillation counting, preferably by scintillation counting by use of $[\gamma\text{-}^{33}\text{P}]\text{ATP}$.

Fractions containing a protein kinase (PK-I, PK-II, PK-III etc) are used in a phosphorylating reaction in the presence of a testing compound under evaluation for fungicidal properties. The method according to the present invention is able to confirm the presence of fungicidal properties when the compound tested has an inhibitory effect on protein kinase activity. If inhibition of the protein kinase activity is observed, the test compound is very probably a fungicide, and to be further tested on pathogens in plants by greenhouse screenings.

This selection test method is useful as a fast screening of compounds that potentially have fungicidal properties.

A preferred assay involves measuring the protein phosphorylating activity by using radioactive $[\gamma\text{-}^{33}\text{P}]\text{ATP}$ and protamine-sulfate as substrate. The phosphorylated products are isolated and quantified by adsorption on P81 chromatography paper and radioactivity measurement in a scintillation counter.

Another aspect of the invention is a fungicide method which comprises applying a fungi inhibiting amount of a protein kinase inhibitor to the locus it is desired to protect from fungi. As used herein, the term "fungi inhibiting amount of protein kinase" refers to an amount of protein kinase inhibitor sufficient to kill or inhibit the fungi it is desired to control. When employed in the treatment of plant fungal diseases, the protein kinase inhibitors are applied to the plants in a disease inhibiting and phytologically acceptable amount. The term "disease inhibiting and phytologically acceptable amount" as used herin, refers to an amount of a compound of the invention which kills or inhibits the plant disease for which control is desired, but is not significantly toxic to the plant.

One aspect of the invention is a fungicide composition comprising a protein kinase inhibitor as the active ingredient in combination with a carrier. When used on plants, protein kinase inhibitors are applied in the form of compositions which are important embodiments of the invention, and which comprise a protein kinase inhibitor as active ingredient in combination with a phytologically-acceptable carrier.

The compositions can be applied to the crop area or plant to be treated, simultaneously or in succession with further compounds. These further compounds can be e.g. fertilisers or micronutrient donors or other preparations which influence the growth of plants. They can also be selective herbicides as well as insecticides, fungicides, bactericides, nematicides, molluscicides or mixtures of several of these preparations, if desired together with further carriers, surfactants or application promoting adjuvants customarily employed in the art of formulation.

The protein kinase inhibitors can be mixed with other fungicides, resulting in some cases in unexpected synergistic activities.

Mixing components which are particularly preferred are azoles such as propiconazole, difenoconazole, cyproconazole, epoxiconazole, tebuconazole, tetraconazole, fenbuconazole, metconazole, bromuconazole; and also fenpropidine, fenpropimorph, cyprodinile, pyrimethanile, S-methyl benzo-1,2,3-thiadiazole-7-thiocarboxylate; and strobilurines such as azoxystrobine and cresoximemethyl.

Suitable carriers and adjuvants can be solid or liquid and are substances useful in formulation technology, e.g. natural or regenerated mineral substances, solvents, dispersants, wetting agents, tackifiers, thickeners, binders or fertilisers.

A preferred method of applying a protein kinase inhibitor, or an agrochemical composition which contains at least one of said compounds, is foliar application. The frequency of application and the rate of application will depend on the risk of infestation by the corresponding pathogen. However, the compounds of formula I can also penetrate the plant through the roots via the soil (systemic action) by drenching the locus of the plant with a liquid formulation, or by applying the compounds in solid form to the soil, e.g. in granular form (soil application). In crops of water rice such granulates can be applied to the flooded rice field. The protein kinase inhibitor may also be applied to seeds (coating) by impregnating the seeds or tubers either with a liquid formulation of the fungicide or coating them with a solid formulation.

The protein kinase inhibitor are used in unmodified form or, preferably, together with the adjuvants conventionally employed in the art of formulation. To this end they are conveniently formulated in known manner to emulsifiable concentrates, coatable pastes, directly sprayable or dilutable solutions, dilute emulsions, wettable powders, soluble powders, dusts, granulates, and also encapsulations e.g. in polymeric substances. As with the type of the compositions, the methods of application, such as spraying, atomising, dusting, scattering, coating or pouring, are chosen in accordance with the intended objectives and the prevailing circumstances.

Advantageous rates of application are normally from 5 g to 2 kg of active ingredient (a.i.) per hectare (ha), preferably from 10 g to 1 kg a.i./ha, most preferably from 20 g to 600 g a.i./ha. When used as seed drenching agent, convenient dosages are from 10 mg to 1 g of active substance per kg of seeds.

The formulation, i.e. the compositions containing the protein kinase inhibitor and, if desired, a solid or liquid adjuvant, are prepared in known manner, typically by intimately mixing and/or grinding the compound with extenders, e.g. solvents, solid carriers and, optionally, surface active compounds (surfactants).

Suitable solvents may typically be: aromatic hydrocarbons, preferably the fractions containing 8 to 12 carbon atoms such as xylene mixtures or substituted naphthalenes; phthalates such as dibutyl or dioctyl phthalate; aliphatic hydrocarbons such as cyclohexane or paraffins; alcohols and glycols and their ethers and esters such as ethanol, diethylene glycol, 2-methoxyethanol or 2-ethoxyethanol; ketones such as cyclohexanone; strongly polar solvents such as N-methyl-2-pyrrolidone, dimethyl sulfoxide or dimethyl formamide; as well as vegetable oils or epoxidised vegetable oils such as epoxidised coconut oil or soybean oil; and water.

The solid carriers typically used for dusts and dispersible powders are usually natural mineral fillers such as calcite, talcum, kaolin, montmorillonite or attapulgite. To improve the physical properties it is also possible to add highly dispersed silicic acid or highly dispersed absorbent polymers. Suitable granulated adsorptive carriers are porous types, including pumice, broken brick, sepiolite or bentonite; and suitable nonsorbent carriers are materials such as calcite or sand. In addition, innumerable pregranulated materials of inorganic or organic origin may be used, typically especially dolomite or pulverised plant residues.

Depending on the protein kinase inhibitor to be formulated, suitable surfactants are nonionic, cationic and/or anionic surfactants having good emulsifying, dispersing and wetting properties. Surfactants will also be understood to include surfactant mixtures.

Suitable anionic surfactants may be so-called water-soluble soaps as well as water-soluble synthetic surface-active compounds.

Illustrative examples of nonionic surfactants are nonylphenol polyethoxyethanols, castor oil polyglycol ether, polyadducts of polypropylene and polyethylene oxide, tributylphenoxy polyethoxyethanol, polyethylene glycol and octylphenoxy polyethoxyethanol.

Fatty acid esters of polyoxyethylene sorbitan, such as polyoxyethylene sorbitan trioleate, are also suitable.

The cationic surfactants are preferably quarternary ammonium salts carrying, as N-substituent, at least one $C_8$–$C_{22}$ alkyl radical and, as further substituents, optionally halogenated lower alkyl, benzyl or hydroxy-lower alkyl radicals.

Further surfactants customarily employed in the art of formulation are known to the expert or can be found in the relevant literature.

The agrochemical formulations will usually contain from 0.1 to 99% by weight, preferably from 0.1 to 95% by weight, of the compound of formula I, 99.9 to 1% by weight, preferably 99.8 to 5% by weight, of a solid or liquid adjuvant, and from 0 to 25% by weight, preferably from 0.1 to 25% by weight, of a surfactant.

Whereas it is preferred to formulate commercial products as concentrates, the end user will normally use dilute formulations.

The compositions may also contain further adjuvants such as stabilisers, antifoams, viscosity regulators, binders or tackifiers as well as fertilisers, micronutrient donors or other formulations for obtaining special effects.

Yet another aspect of the invention is a fungicide composition in combination with another fungicide.

The following examples further illustrates the present invention.

EXAMPLE 1
Preparation of Protein Kinase from *Neurospora crassa*

Mycelium from a stock culture of the wild-type strain 74-OR8-1, obtained from the American Type Culture Collection (ATCC 18889), is grown as inoculum in Petri dishes (d=9 cm) at 24° C. in the dark for 14 days (medium: Biomalt 10 g, Difco dry yeast extract 4 g, glucose 4 g and agar 20 g, in 1 l water). Macroconidia are washed off with 10 ml sterile water, filtered through glass wool and then transferred into Erlenmeyer flasks (1 l) containing 500 ml of Vogel's minimal medium to give $5\times10^4$ macroconidia $ml^{-1}$ (medium: tri-sodium citrate dihydrate 150 g, $KH_2PO_4$ 250 g, $NH_4NO_3$ 100 g, $MgSO_4 7H_2O$ 10 g, $CaCl_2 2H_2O$ 5 g, citric acid monohydrate 0.25 g, $ZnSO_4 7H_2O$ 0.25 g, $Fe(NH_4)_2(SO_4)_2 6H_2O$ 50 mg, $CuSO_4 5H_2O$ 12.5 mg, $MnSO_4 H_2O$ 2.5 mg, $H_3BO_3$ 2.5 mg, $Na_2MoO_4 2H_2O$ 2.5 mg and sucrose 20 g, in 1 l water). The flasks are incubated on a rotary shaker (150 rev. $min^{-1}$) at 24° C. for 36 hours in the dark. The wet weight of the cells thus obtained from each flask is 50 g. Mycelia (50 g) are collected by filtration, rinsed with cold water, homogenized with a Sorvall Omni-mixer over 60 seconds and extracted with 100 ml of buffer A: 20 mM Tris-HCl (pH 7.6), 10 mM EGTA, 2 mM EDTA, 50 mM 2-mercaptoethanol, 0.25 M sucrose, 0.3 mM $NaN_3$, 10 mM benzamidine, 1 mM phenylmethylsulfonyl fluoride, 0.25 μg $ml^{-1}$ pepstatin, 10 μg $ml^{-1}$ leupeptin. The homogenate is centrifuged at 200000 g for 20 min. The supernatant is further centrifuged at 100000 g for 1 hour. The pellet is discarded and the supernatant is collected through glass wool and solid $(NH_4)SO_4$ is added to a final level of 50% saturation. The precipitate is recovered by centrifugation at 20000 g for 20 min and resuspended in 2.5 ml buffer B: 20 mM tris-HCl (pH 7.6), 1 mM EGTA, 1 mM EDTA, 50 mM 2-mercaptoethanol. The suspension is then successively passed through a Sephadex G-25 PD-10 and applied to a Bio-Gel TSK DEAE-5-PW column (75×7.5 mm) equilibrated with buffer B. The column is extensively washed with the same buffer. Adsorbed proteins are eluted at a linear gradient of NaCl (0–0.4 M) added in buffer B. Fractions of 2 ml are collected and assayed for protein kinase activity. The active fractions are desalted on Sephadex G-25 PD-10. On the assumption that protein kinases like other nucleoside-binding enzymes bind to the chromophoric group of Cibacron Blue® F3GA dye, fractions containing active protein kinases are chromatographed on Affi-Gel® Blue gel (Bio-Rad Laboratories). The column (1×6 cm) is equilibrated with buffer B. The enzymes are then adsorbed and 20 ml of buffer B is allowed to pass through. Protein kinases are eluted with a linear gradient of 0–0.4 M NaCl in buffer B. 2 ml fractions are collected and assayed for protein kinase activity.

Three protein kinases activities (PK-I, PK-II and PK-III) are found in the supernatant of *N.crassa* by using protamine-sulfate as substrate.

EXAMPLE 2
Protein Kinase Assay

Protein kinase activity is assayed in a reaction mixture containing in a final volume of 100 ml, 20 mM Tris-HCl (pH 7.4), 20 mg protamine-sulfate, 10 mM $Mg(NO_3)_2$, 10 mM ATP (0.2 mCi [g-$^{33}$P]ATP), 1 mM $NaN_3$, 0.04 mM okadaic acid, 20 ml of protein kinase. After 20 minutes incubation at 32° C., aliquots of 50 ml are analyzed for substrate phosphorylation using P81 chromatography paper (20 mm×20 mm; Whatman, Maidstone, UK) according to the method described by J. J. Witt and R. Roskoski (Anal. Biochem., 66, 253–258, 1975). After washing the unbounded radioactivity with 75 mM phosphoric acid (3×15 min) and ethanol 94% (1×5 min) the radioactivity in the chromatography paper is counted in 5 ml ULTIMA GOLD LSC-cocktail (Packard Instrument, Zürich, Switzerland) using a Tri-Carb 2500 TR Packard Instrument.

EXAMPLE 3
Protein Kinase Inhibition Assay

To identify potential fungicides a protein kinase inhibition assay is carried out as follows: Protein kinase inhibition measurement is carried out by using the protein kinase assay as described above except that various concentrations of inhibitors are added in the incubation medium from 20-fold concentrated stock solutions in dimethylsulfoxide. Control treatments contain equivalent quantities of dimethylsulfoxide. Inhibition rate is calculated in relation to the control test (=0% inhibition) and the $IC_{50}$ value (concentration of inhibitor required to reduce activity by 50%) is used as parameter for inhibition.

Results

Addition of 100 μM fenpiclonil=4-(2,3-dichlorophenyl) pyrrole-3-carbonitrile in the enzyme assay mixture reveals the phenylpyrrole sensitivity of the protein kinases PK-III (90% inhibition) and PK-II (67% inhibition) (FIG. 1).

BRIEF DESCRIPTION OF THE DRAWING

FIG. 1 shows the result of a DEAE-TSK separation of protein kinases from *Neurospora crassa* measured with protamine sulfate as substrate in the absence (dark symbols) and in the presence (white symbols) of 100 mM fenpiclonil. (–) NaCl gradient (0–0.4 M).

What is claimed is:

1. A method for identifying potential fungicides which comprises testing a test substance in a protein kinase inhibition assay said assay comprising:

a) preparing an assay mixture consisting essentially of a phosphate acceptor, magnesium nitrate, a phosphate donor, $NaN_3$, okadaic acid, and a suitable protein kinase, in the presence of an appropriate solvent, which protein kinase has been isolated from a fungus, and which is active in said assay in the absence of an inhibitor thereto;

b) determining the activity of said protein kinase in the presence of: (i) a test substance, (ii) a device for measuring the phosphorylation rates; and c) selecting test substances which inhibit the protein kinase, wherein inhibition of protein kinase activity is indicative of fungicidal activity.

2. The method of claim 1 wherein the phosphate acceptor is selected from casein, histone, kemptide, protamine free base and protamine-salt.

3. The method according to claim 1 wherein the phosphate acceptor is protamine sulfate.

4. The method according to claim 1 in which the phosphate donor used is radioactive [γ-$^{33}$P]ATP.

5. The method according to claim 1 wherein the ATP is radioactive [γ-$^{33}$P]ATP and the device is a scintillation counter.

6. The method according to claim 1 in which said appropriate solvent is dimethylsulfoxide.

7. The method of claim 1 wherein said protein kinase is a protein kinase III from *Neurospora crassa*.

8. The method of claim 1, further comprising testing the compound for activity against fungi.

* * * * *